(12) United States Patent
Di-Drusco et al.

(10) Patent No.: US 6,355,227 B1
(45) Date of Patent: Mar. 12, 2002

(54) ORAL COMPOSITION

(75) Inventors: Isotta Di-Drusco, Gaggiano (IT); Derek Michael Hull, Bebington Wirral (GB)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/586,088

(22) Filed: Jun. 2, 2000

(30) Foreign Application Priority Data

Jun. 4, 1999 (EP) .............................. 99201786

(51) Int. Cl.⁷ ................................. A61K 7/16
(52) U.S. Cl. .......................................... 424/49
(58) Field of Search ...................... 424/49–58

(56) References Cited

U.S. PATENT DOCUMENTS

| | | | | |
|---|---|---|---|---|
| 3,985,668 A | * | 10/1976 | Hartman | 259/99 |
| 4,051,055 A | * | 9/1977 | Trinh et al. | 252/95 |
| 4,051,056 A | * | 9/1977 | Hartman | 252/99 |
| 4,240,919 A | * | 12/1980 | Chapman | 252/95 |
| 4,457,856 A | * | 7/1984 | Mitchell et al. | 252/166 |
| 4,526,701 A | * | 7/1985 | Rubin | 252/113 |
| 4,786,369 A | * | 11/1988 | Kanfer et al. | 252/120 |
| 4,786,432 A | * | 11/1988 | Kanfer et al. | 252/120 |
| 5,124,143 A | | 6/1992 | Muhlemann et al. | |
| 5,266,304 A | | 11/1993 | Baffelli et al. | |
| 5,597,553 A | | 1/1997 | Baffelli et al. | |
| 5,976,506 A | * | 11/1999 | Vernon | 424/49 |
| 6,010,683 A | * | 1/2000 | Fischer, et al. | 424/52 |
| 6,083,489 A | * | 7/2000 | Fischer, et al. | 424/52 |
| 6,139,820 A | * | 10/2000 | Fischer, et al. | 424/52 |

FOREIGN PATENT DOCUMENTS

| | | |
|---|---|---|
| EP | 0 268 763 | 9/1987 |
| EP | 0 528 756 | 7/1992 |
| JP | 11152216 A * | 6/1999 |
| WO | 94/15577 | 7/1994 |
| WO | 96/09034 | 3/1996 |

* cited by examiner

*Primary Examiner*—Shep K. Rose
(74) *Attorney, Agent, or Firm*—Milton L. Honig

(57) ABSTRACT

An oral composition comprises perlite, characterised in that it comprises from 0.01 to 0.9% by weight perlite.

7 Claims, No Drawings

ORAL COMPOSITION

BACKGROUND OF THE INVENTION

1. Field of the Invention

This invention relates to an oral composition comprising low levels of perlite.

2. The Related Art

The inclusion of abrasives in oral compositions such as toothpaste is well known. The abrasive has a cleaning as well as a polishing/whitening benefit. The removal of tartar from the tooth surface is thought to reduce the incidence of caries.

Dental Practitioners recommend that tartar removal should be exercised professionally at least twice a year, preferably more but it is recognised that the build-up of tartar can be reduced by effective brushing of the teeth.

Typical abrasives used in toothpastes include silicas and chalk, however, the prior art also discloses the use of perlite in toothpaste formulations. EP-B1-0 268 763 (Hawe-Neos) describes a dental care medium for prophylactic dental hygiene comprising perlite and a synthetically produced precipitation silicic acid. U.S. Pat. No. 5,266,304 (Baffelli) describes dental care and cleaning composition in a water-free part containing at least 40% by weight of perlite as a sole and combined cleaning and polishing body. U.S. Pat. No. 5,597,553 (Baffelli) describes a toothpaste comprising as an abrasive, preferably as sole abrasive, expanded perlite, generally with a particle size in the range of 1 to 150 $\mu$m, in particular with main fraction in the region 20 $\mu$m. The perlite is comprises from 1 to not more than 15% by weight of the composition.

The abrasivity of a toothpaste is measured according to a protocol described in the journal of Dental Research (1976) 55(4), 563. This describes how the Relative Dental Abrasion (RDA) and Relative Enamel Abrasion (REA) are evaluated.

Ideally, a toothpaste will be capable of cleaning the teeth without wearing down the tooth enamel and dentine. So while it is necessary to have a cleaning efficacy a toothpaste with too high an RDA is undesirable. In Advanced Dental Research Vol 11, (4) pp576–579 is described a method for evaluating the Pellicle Cleaning Ratio (PCR) which is commonly used as a measure of cleaning.

The use of high quantities of perlite also has its disadvantages. Perlite is a natural product and while it is purified to a reasonable degree before incorporation into an oral care formulation it still comprises impurities. These impurities are usually of a grey colour and introduce speckling of the formulation. This is particularly noticeable where the product is a white paste. Again, this is seen as a significant consumer negative. A further disadvantage of high levels of perlite is that it behaves as a catalyst for the degradation of flavour ingredients, particularly in products where the pH is relatively high, e.g. in oral compositions comprising bicarbonate. This is a clear disadvantage for the consumer but is also unacceptable for the manufacturer as the cost of the flavour often accounts for the bulk of the raw materials costs. It is also known for high quantities of perlite to cause syneresis of typical dentifrice formulations.

SUMMARY OF THE INVENTION

We have surprisingly found that perlite can be incorporated as a cleaning agent in smaller amounts than is disclosed in the prior art, while still providing an effective cleaning benefit. Further the abrasive effect of the reduced levels of perlite also provide for a greater cleaning/polishing with respect to abrasivity than higher quantities of perlite, i.e. the PCR substantially maintained or reduced only partially, while the RDA is significantly reduced by using smaller amounts of perlite.

Accordingly, the invention provides an oral composition comprising from 0.01 to 0.9% by weight of perlite.

Preferably, the composition according to the invention comprises from 0.1 to 0.8% and especially from 0.3 to 0.7% by weight of perlite.

DETAILED DESCRIPTION OF THE INVENTION

Perlite is a naturally occurring sodium/potassium/aluminium silicate and is available commercially from Seitzfilterwerke as Perlite C; from Elfatochem as Ceka Flo MA/P/2A/R; and from World Mineral as Europearl 475/900S/E50.

A preferred perlite comprises particles of average size below 300 and preferably below 200 $\mu$m in diameter. It is understood that the size reference to diameter is approximate as the particles are of random shape and not necessarily spherical. If a sample comprises larger particles of perlite it is preferred that the sample is sieved through a suitable gauge before being included in the formulation.

The composition according to the invention may be any oral, non-food composition, e.g. toothpaste and may be in the form of a gel, paste, gum or any other suitable type.

The composition according to the invention may also comprise ingredients, which are common in dentifrices. Examples of such ingredients include:

antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium-, calcium-, magnesium- and stannous fluoride, aminefluorides, disodium monofluorophosphate, sodium trimeta phosphate and casein;

plaque buffers such as urea, calcium lactate, calcium glycerophosphate and strontium polyacrylates;

vitamins such as Vitamin C;

plant extracts;

desensitising agents, e.g. potassium citrate, potassium chloride, potassium tartrate, potassium bicarbonate, potassium oxalate, potassium nitrate and strontium salts;

anti-calculus agents, e.g. hypophosphite-containing polymers, organic phosphonates and phosphocitrates etc.;

gum protection agents, e.g. vegetable oils such as sunflower oil, rape seed oil, soybean oil and safflower oil; silicone oil; and hydrocarbon oil. The gum protection agent may be an agent capable of improving the permeability barrier of the gums. A complete description of agents capable of improving the permeability barrier of the gum is found in our co-pending application GB 9810521;

biomolecules, e.g. bacteriocins, antibodies, enzymes, etc.;

flavours, e.g. peppermint and spearmint oils;

preservatives;

opacifying agents;
colouring agents;
pH-adjusting agents;
sweetening agents;
pharmaceutically acceptable carriers, e.g. starch, sucrose, water or water/alcohol systems etc.;
surfactants, such as anionic, nonionic, cationic and zwitterionic or amphoteric surfactants;
particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials;
humectants such as glycerol, sorbitol, propyleneglycol, xylitol, lactitol etc.;
binders and thickeners such as sodium carboxymethylcellulose, xanthan gum, gum arabic etc. as well as synthetic polymers such as polyacrylates and carboxyvinyl polymers such as Carbopol®;
buffers and salts; and
other optional ingredients that may be included are e.g. bleaching agents such as peroxy compounds e.g. potassium peroxydiphosphate, effervescing systems such as sodium bicarbonate/citric acid systems, colour change systems, and so on.

The oral composition may also be in any of the product forms common in the art, e.g. dentifrice (gel or paste), lozenge, chewing gum etc.

The invention is described further by reference to the following non-limiting examples:

EXAMPLE 1

The following is a formulation according to the invention and is made by conventional methods.

| Ingredient | Amount (% by weight) |
| --- | --- |
| Potassium tetrapyrophosphate | 3.00 |
| Glycerin | 30.00 |
| Sodium fluoride | 0.32 |
| Sodium saccharin | 0.25 |
| Polyethylene glycol | 4.00 |
| Titanium dioxide | 1.00 |
| Thickening silica | 8.00 |
| Abrasive silica | 8.00 |
| Bicarbonate | 8.00 |
| Perlite | 0.70 |
| SLS | 1.80 |
| Flavour | 1.00 |
| Water | to 100% |

EXAMPLE 2

The following table shows the PCR and RDA of typical dentifrice formulations comprising varying levels of perlite.

It can be clearly seen that by reducing the level of perlite from 3% to 0.5 by weight of the composition the PCR can be maintained at 93% while the abrasivity is reduced to 78%.

| Perlite % w/w | RDA | PCR | RDA/PCR |
| --- | --- | --- | --- |
| 0.5 | 78 | 91 | 0.85 |
| 3.0 | 100 | 98 | 1.02 |

What is claimed is:

1. An oral composition comprising perlite, characterised in that it comprises from 0.01 to 0.9% by weight perlite.

2. Oral composition according to claim 1, characterised in that it comprises from 0.1 to 0.8% by weight perlite.

3. Oral composition according to claim 1, characterised in that it comprises from 0.3 to 0.7% by weight perlite.

4. An oral composition comprising:

(i) from 0.01 to 0.9% by weight perlite;

(ii) an effective amount to control caries of a fluoride agent selected from the group consisting of sodium fluoride, stannous fluoride and disodium monofluorophosphate; and (iii) a pharmaceutically acceptable carrier.

5. An oral composition comprising:

(i) from 0.01 to 0.7% by weight perlite;

(ii) an effective amount to control caries of a fluoride agent selected from the group consisting of sodium fluoride, stannous fluoride and disodium monofluorophosphate; and (iii) a pharmaceutically acceptable carrier.

6. A method for cleaning teeth comprising applying to the teeth an oral composition comprising:

(i) from 0.01 to 0.9% by weight perlite;

(ii) an effective amount to control caries of a fluoride agent selected from the group consisting of sodium fluoride, stannous fluoride and disodium monofluorophosphate; and (iii) a pharmaceutically acceptable carrier.

7. The method according to claim 6 wherein the perlite is present in an amount from 0.01 to 0.7% by weight.

* * * * *